US011305053B2

(12) United States Patent
Claus et al.

(10) Patent No.: US 11,305,053 B2
(45) Date of Patent: Apr. 19, 2022

(54) SURGICAL HANDPIECE HAVING DIRECTIONAL FLUID CONTROL CAPABILITIES

(71) Applicant: Johnson & Johnson Surgical Vision, Inc., Irvine, CA (US)

(72) Inventors: Michael J Claus, Newport Coast, CA (US); Mitchell W Mallough, Irvine, CA (US)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 30 days.

(21) Appl. No.: 13/772,803

(22) Filed: Feb. 21, 2013

(65) Prior Publication Data

US 2013/0317417 A1 Nov. 28, 2013

Related U.S. Application Data

(60) Provisional application No. 61/651,751, filed on May 25, 2012.

(51) Int. Cl.
*A61M 3/00* (2006.01)
*A61F 9/007* (2006.01)

(52) U.S. Cl.
CPC .......... *A61M 3/00* (2013.01); *A61F 9/00745* (2013.01)

(58) Field of Classification Search
CPC .. A61F 9/00745; A61F 9/00736; A61F 9/007; A61F 2009/00887; A61F 2009/0087; A61M 3/00; A61M 2210/0612; A61M 1/0058; A61M 1/0035; A61M 1/0064; A61M 1/0039; A61M 1/0084;
(Continued)

(56) References Cited

U.S. PATENT DOCUMENTS 3,081,770 A * 3/1963 Hunter .......................... 600/431
4,168,707 A * 9/1979 Douvas et al. ................. 604/32
(Continued)

FOREIGN PATENT DOCUMENTS

| WO | 0219896 A2 | 3/2002 |
| WO | WO 2009036818 A1 * | 3/2009 |
| WO | 2013176713 A1 | 11/2013 |

OTHER PUBLICATIONS

"variable." Dictionary.com. 2019. https://www.dictionary.com/browse/variable (Jan. 10, 2019).*

(Continued)

*Primary Examiner* — Scott J Medway
(74) *Attorney, Agent, or Firm* — Johnson & Johnson Surgical Vision, Inc.

(57) ABSTRACT

A medical system is provided having a system host and a control device connected to the system host. The medical system further includes a handpiece having a sleeve with a port opening configured to enable fluid to pass there through, a fluid channel connected to the port opening, and a fluid flow restrictor configured to restrict fluid flow of the fluid channel through the port opening. The control unit is configured to receive input from a user and control an amount of fluid provided by the fluid flow restrictor based on the input received from the user. In one aspect, the medical system is a phacoemulsification system, the handpiece a phacoemulsification handpiece, and the control device a footpedal.

22 Claims, 8 Drawing Sheets

(58) Field of Classification Search
CPC ........ A61M 3/0254; A61M 2039/2473; A61M 25/0029; A61B 2217/007; A61B 2218/002
USPC ................. 606/4, 6, 107, 167, 1; 604/44
See application file for complete search history.

(56) References Cited

U.S. PATENT DOCUMENTS

| | | | |
|---|---|---|---|
| 4,180,068 A * | 12/1979 | Jacobsen et al. | 604/44 |
| 4,331,130 A * | 5/1982 | Lewicky | 604/23 |
| 4,515,583 A | 5/1985 | Sorich | |
| 4,768,547 A * | 9/1988 | Danby et al. | 137/454.4 |
| 4,983,901 A | 1/1991 | Lehmer | |
| 5,112,339 A * | 5/1992 | Zelman | 606/107 |
| 5,242,404 A * | 9/1993 | Conley et al. | 604/119 |
| 5,261,883 A * | 11/1993 | Hood et al. | 604/153 |
| 5,268,624 A | 12/1993 | Zanger | |
| 5,279,549 A * | 1/1994 | Ranford | A61M 1/0043 604/34 |
| 5,342,293 A | 8/1994 | Zanger | |
| 5,545,161 A * | 8/1996 | Imran | A61B 18/1492 606/41 |
| 5,569,188 A * | 10/1996 | Mackool | 604/67 |
| 5,660,205 A * | 8/1997 | Epstein | A61M 39/24 137/512.15 |
| 5,733,256 A * | 3/1998 | Costin | 604/22 |
| 5,782,806 A * | 7/1998 | Knapp | A61M 1/0058 604/131 |
| 5,792,140 A * | 8/1998 | Tu | A61B 18/08 606/41 |
| 5,885,243 A * | 3/1999 | Capetan et al. | 604/27 |
| 5,971,968 A * | 10/1999 | Tu | A61M 25/007 604/103.01 |
| 5,984,904 A | 11/1999 | Steen et al. | |
| 5,997,499 A * | 12/1999 | Sussman et al. | 604/27 |
| 6,042,586 A * | 3/2000 | Kawano et al. | 606/107 |
| 6,050,986 A * | 4/2000 | Hektner | A61M 5/00 604/264 |
| 6,051,011 A * | 4/2000 | Weidenbenner | 606/171 |
| 6,179,829 B1 * | 1/2001 | Bisch | A61C 1/0023 200/51.02 |
| 6,258,111 B1 * | 7/2001 | Ross et al. | 606/171 |
| 6,260,434 B1 | 7/2001 | Holtorf | |
| 6,360,630 B2 | 3/2002 | Holtorf | |
| 6,452,120 B1 | 9/2002 | Chen | |
| 6,452,123 B1 | 9/2002 | Chen | |
| 6,659,740 B2 * | 12/2003 | Drevet | 417/436 |
| 6,674,030 B2 | 1/2004 | Chen et al. | |
| 6,979,328 B2 * | 12/2005 | Baerveldt et al. | 606/41 |
| 7,509,831 B2 * | 3/2009 | Khashayar | 73/1.72 |
| 7,625,388 B2 * | 12/2009 | Boukhny et al. | 606/169 |
| 7,695,447 B2 * | 4/2010 | Khashayar et al. | 604/27 |
| 8,291,933 B2 * | 10/2012 | Bourne et al. | 137/533.11 |
| 8,721,594 B2 * | 5/2014 | Zacharias | 604/119 |
| 8,753,323 B2 * | 6/2014 | Urich et al. | 604/320 |
| 8,758,433 B2 * | 6/2014 | Cole et al. | 623/6.12 |
| 8,814,543 B2 * | 8/2014 | Liebing | 417/436 |
| 9,642,962 B2 * | 5/2017 | Matson | A61M 25/003 |
| 10,512,718 B2 * | 12/2019 | Shtul | A61B 1/31 |
| 2001/0020401 A1 | 9/2001 | Holtorf | |
| 2004/0204735 A1 * | 10/2004 | Shiroff | A61B 17/320016 606/190 |
| 2005/0054971 A1 * | 3/2005 | Steen et al. | 604/22 |
| 2005/0228423 A1 * | 10/2005 | Khashayar et al. | 606/167 |
| 2005/0228424 A1 * | 10/2005 | Khashayar et al. | 606/167 |
| 2007/0005002 A1 * | 1/2007 | Millman et al. | 604/30 |
| 2008/0161792 A1 * | 7/2008 | Wang | A61B 18/1492 606/41 |
| 2008/0289398 A1 | 11/2008 | Khashayar | |
| 2008/0319374 A1 * | 12/2008 | Zacharias | 604/22 |
| 2009/0234193 A1 * | 9/2009 | Weisenburgh, II | A61B 1/00068 600/157 |
| 2010/0057092 A1 * | 3/2010 | Peterson | 606/107 |
| 2010/0076471 A1 * | 3/2010 | Bourne et al. | 606/161 |
| 2010/0185150 A1 * | 7/2010 | Zacharias | 604/119 |
| 2010/0191178 A1 * | 7/2010 | Ross et al. | 604/22 |
| 2011/0184348 A1 * | 7/2011 | Bates et al. | 604/131 |
| 2012/0157912 A1 * | 6/2012 | Sorensen et al. | 604/28 |
| 2012/0289892 A1 * | 11/2012 | Shtul | A61B 1/31 604/28 |
| 2014/0257172 A1 * | 9/2014 | Yalamanchili | 604/22 |
| 2015/0157501 A1 * | 6/2015 | Bourne et al. | |

OTHER PUBLICATIONS

International Search Report and Written Opinion for Application No. PCT/US2013/027057, dated Jun. 18, 2013, 11 pages.

* cited by examiner

SURGICAL HANDPIECE HAVING DIRECTIONAL FLUID CONTROL CAPABILITIES

CROSS-REFERENCE TO RELATED APPLICATIONS

This application claims priority to U.S. provisional application No. 61/651,751, entitled "Surgical Handpiece Having Directional Fluid Control Capabilities", filed on May 25, 2012, the entire contents of which are hereby incorporated by reference in their entirety for all purposes as if fully set forth herein.

BACKGROUND OF THE INVENTION

I. Field

The present invention generally relates to fluid delivery using handpieces and more specifically to directional handpiece irrigation and/or aspiration control during surgical procedures.

II. Description of the Related Art

Phacoemulsification refers to a method of lens and cataract extraction from an eye. The procedure includes an ultrasonically vibrated needle which is inserted through a very small incision in the cornea in order to provide energy for fragmenting the lens and cataract which then can be aspirated and removed through the incision.

The needle is supported by a handpiece interconnected with a console which provides electrical power to the handpiece as well as a supply of irrigation fluid used to irrigate or provide fluid to the eye and a vacuum source for aspiration or removal of fragmented tissue and liquids.

Certain current handpieces can provide fluid to the eye during the surgical procedure. In general, at least one port is provided in the handpiece, frequently in the sleeve of the handpiece, and two ports are sometimes provided. Flow issues can arise when the surgeon wishes to control the direction of fluid flow, either using irrigation or aspiration.

Surgeons must be careful with fluid flow in that fluid flow directed toward certain parts of the eye chamber, such as the retina or cornea, can potentially harm those regions. Further, some surgeons wish to employ the fluid in conjunction with the needle to more rapidly acquire and/or break apart the unwanted cataract materials. Such surgeons employ fluid flow and ultrasonic power in tandem, and if the surgeon does not know the orientation of fluid flow, he runs the risk of moving the fluid in an undesired direction, for example pushing away material he wishes to work on and break up. Such an occurrence could potentially extend the duration of the surgery, and is undesirable.

In efforts to address these flow issues, surgeons have on occasion moved the handpiece such that the port arrangement provides flow in the desired direction. The result of such movement can be repositioning the needle into an undesirable orientation. Alternately, the surgeon can simply work with the flow provided, potentially causing a random flow of fluid that does not accomplish the desired irrigation task. The result is a partially or even completely obscured field resulting from the swirling of emulsified material, a phenomenon referred to as "milking" or "clouding." Each of the foregoing situations, wherein constant fluid flow direction is provided, is less than ideal.

One further issue with such devices is controlling the fluid. Fluid control can be difficult in that the surgeon is performing a delicate procedure, and requiring her to engage a button on the handpiece or a button on a console would likely interrupt the procedure and/or require an inordinate amount of control and dexterity. Controlling direction may take more than pushing a single on/off button, but instead may require multiple directional inputs and potentially an input controlling flow rate or volume. As a result, devices to control fluid direction could be highly complicated and could potentially require actions by another person, or inordinately excessive dexterity or manual actions by the surgeon. Again, such situations are unacceptable, particularly in a surgical environment where patient safety and surgeon concentration are paramount considerations.

It would therefore be desirable to provide a phacoemulsification fluid irrigation and aspiration design, including an apparatus to control irrigation and aspiration direction that minimizes the adverse aspects previously known in such devices.

SUMMARY

The following presents a simplified summary in order to provide a basic understanding of some aspects of the claimed subject matter. This summary is not an extensive overview, and is not intended to identify key/critical elements or to delineate the scope of the claimed subject matter. Its sole purpose is to present some concepts in a simplified form as a prelude to the more detailed description that is presented later.

The present invention includes a medical system having a system host and a control device connected to the system host. The medical system further includes a handpiece having a sleeve with a port opening configured to enable fluid to pass therethrough, a fluid channel connected to the port opening, and a fluid flow restrictor configured to restrict fluid flow of the fluid channel through the port opening. The control unit is configured to receive input from a user and control an amount of fluid provided by the fluid flow restrictor based on the input received from the user. In one aspect, the medical system is a phacoemulsification system, the handpiece a phacoemulsification handpiece, and the control device a dual axis footpedal.

To the accomplishment of the foregoing and related ends, certain illustrative aspects are described herein in connection with the following description and the annexed drawings. These aspects are indicative, however, of but a few of the various ways in which the principles of the claimed subject matter may be employed and the claimed subject matter is intended to include all such aspects and their equivalents. Other advantages and novel features may become apparent from the following detailed description when considered in conjunction with the drawings.

DETAILED DESCRIPTION

Figure 1:
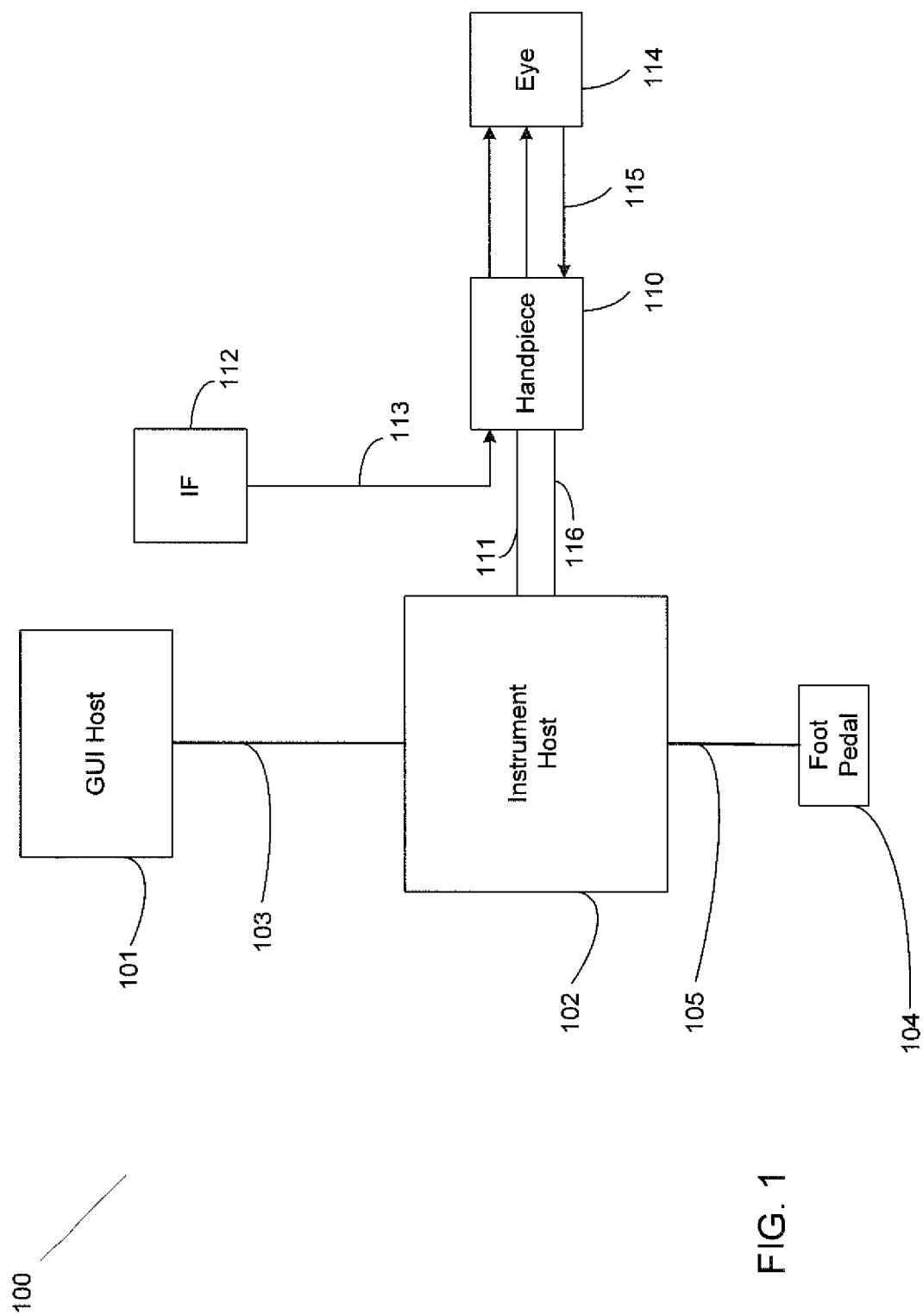
FIG. 1 is a general depiction of a medical system in accordance with an embodiment of the present design.

In this document, the words "embodiment," "variant," and similar expressions are used to refer to particular apparatus, process, or article of manufacture, and not necessarily to the same apparatus, process, or article of manufacture. Thus, "one embodiment" (or a similar expression) used in one place or context can refer to a particular apparatus, process, or article of manufacture; the same or a similar expression in a different place can refer to a different apparatus, process, or article of manufacture. The expression "alternative embodiment" and similar phrases are used to indicate one of a number of different possible embodiments. The number of possible embodiments is not necessarily limited to two or any other quantity.

The word "exemplary" is used herein to mean "serving as an example, instance, or illustration." Any embodiment or variant described herein as "exemplary" is not necessarily to be construed as preferred or advantageous over other embodiments or variants. All of the embodiments and variants described in this description are exemplary embodiments and variants provided to enable persons skilled in the art to make or use the invention, and not to limit the scope of legal protection afforded the invention, which is defined by the claims and their equivalents.

The present design includes a controllable fluid flow restrictor arrangement in connection with a phacoemulsification handpiece, wherein fluid lines can be selectively blocked by a surgeon or operator to control both the amount of fluid flow and the direction of fluid flow in aspiration and/or irrigation situations. The design includes impeding the fluid path on a selective basis, such as partially or completely closing a fluid path as desired. The present design may be operated using a control device such as a footpedal, in one embodiment a dual axis footpedal, wherein surgeon foot movement in the pitch direction of the dual axis footpedal can, in one example, control fluid flow by opening and closing one flow restrictor and movement in the yaw axis can control fluid flow by opening and closing a second flow restrictor, thus controlling the amount of fluid provided to or from ports provided on the handpiece. Control may alternately be provided by other devices, such as a single axis footpedal, where fluid direction is controlled in the pitch direction as well as side switches, for example. Side switches may be switches engageable by the surgeon's foot provided on the side of the footpedal, where the surgeon taps the side switch to increase flow in increments in a given direction or otherwise control fluid flow.

System Example

While the present design may be used in various environments and applications, it will be discussed herein with a particular emphasis on an environment where a surgeon or health care practitioner performs. For example, one embodiment of the present design is in or with an ocular surgical system that comprises an independent graphical user interface (GUI) host module, an instrument host module, a GUI device, and a controller module, such as a foot pedal, to control the surgical system.

FIG. 1 illustrates an exemplary phacoemulsification/vitrectomy system 100 in a functional block diagram to show the components and interfaces for a safety critical medical instrument system that may be employed in accordance with an aspect of the present invention. A serial communication cable 103 connects GUI host 101 module and instrument host 102 module for the purposes of controlling the surgical instrument host 102 by the GUI host 101. Instrument host 102 may be considered a computational device in the arrangement shown, but other arrangements are possible. An interface communications cable (not shown) may be connected to instrument host 102 module for distributing instrument sensor data, and may include distribution of instrument settings and parameters information, to other systems, subsystems and modules within and external to the instrument host 102 module. An interface communications cable may be connected or realized on any other subsystem (not shown) that could accommodate such an interface device able to distribute required data.

A switch module associated with foot pedal 104 may transmit control signals relating internal physical and virtual switch position information as input to the instrument host 102 over serial communications cable 105. A wireless footpedal may alternately be provided. Instrument host 102 may provide a database file system for storing configuration parameter values, programs, and other data saved in a storage device (not shown). In addition, the database file system may be realized on the GUI host 101 or any other subsystem (not shown) that could accommodate such a file system.

The example system 100 in FIG. 1 has a handpiece 110 that includes a needle and electrical means, typically a piezoelectric crystal, for ultrasonically vibrating the needle. The instrument host 102 supplies power on line 111 to a phacoemulsification/vitrectomy handpiece 110. An irrigation fluid source 112 can be fluidly coupled to handpiece 110 through line 113. The irrigation fluid and ultrasonic power are applied by handpiece 110 to an eye, or affected area or region, indicated diagrammatically by block 114. Alternatively, the irrigation source may be routed to eye 114 through a separate pathway independent of the handpiece. Aspiration is provided to eye 114 by a pump (not shown), such as a peristaltic pump and/or Venturi pump, via the instrument host 102, through lines 115 and 116. A surgeon/operator may select an amplitude of electrical pulses using the handpiece, or via the instrument host and GUI host, or using a footpedal or switch provided on a footpedal.

FIG. 1 represents an example design that may employ the present invention, but other implementations are possible. For example, rather than a phacoemulsification or vitrectomy handpiece, the present design may be provided on a device that simply controls fluid, called an I/A (Irrigation/Aspiration) handpiece. (Irrigation/Aspiration) employed together with a handpiece comprising a needle, where the second handpiece may include fluid irrigation and/or aspiration functionality.

Handpiece Design

Figure 2:
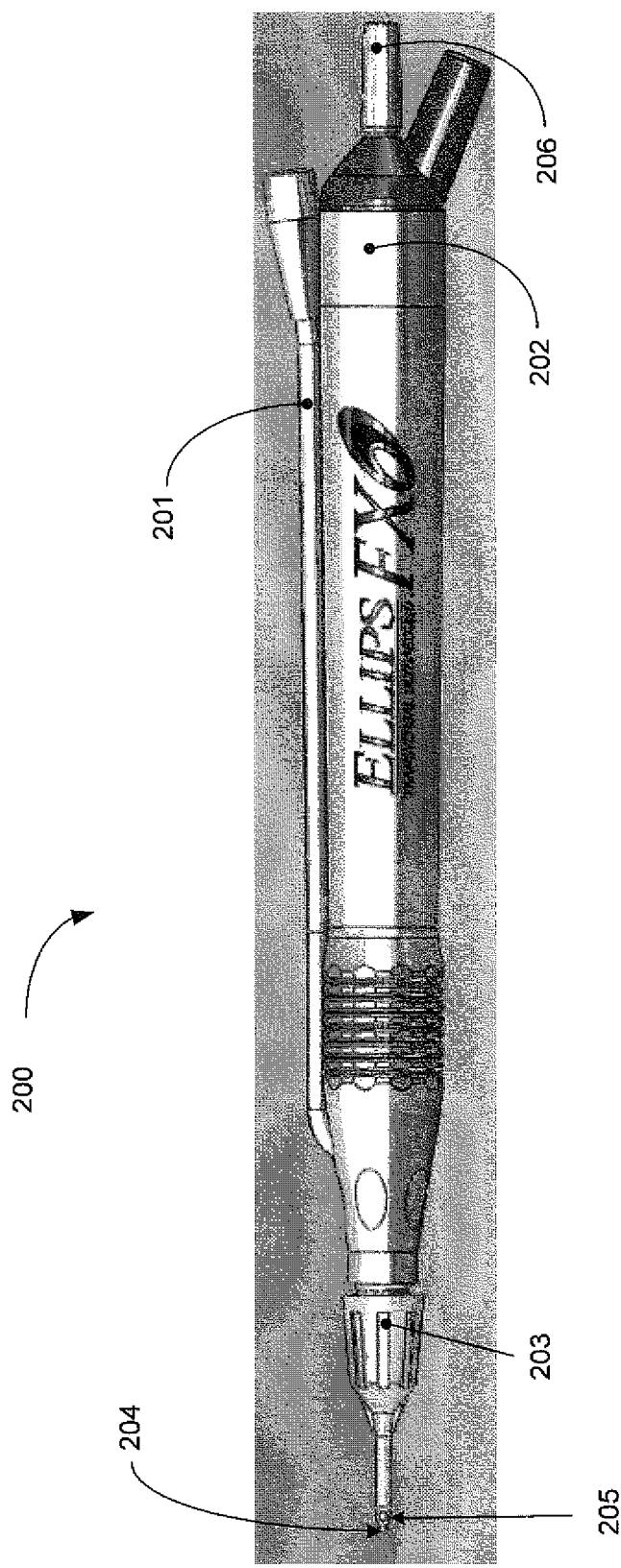
FIG. 2 illustrates a representative handpiece that may be employed with the present design.

FIG. 2 illustrates a representative handpiece 200 having similarity to the handpiece of the present design. From FIG. 2, handpiece 200 includes fluid line 201, base 202, and includes sleeve 203. Sleeve 203 houses the needle 204, partially shown through the port 205 near the tip of sleeve 203. Aspiration line 206 is used to remove fluid from the site.

Figure 3:
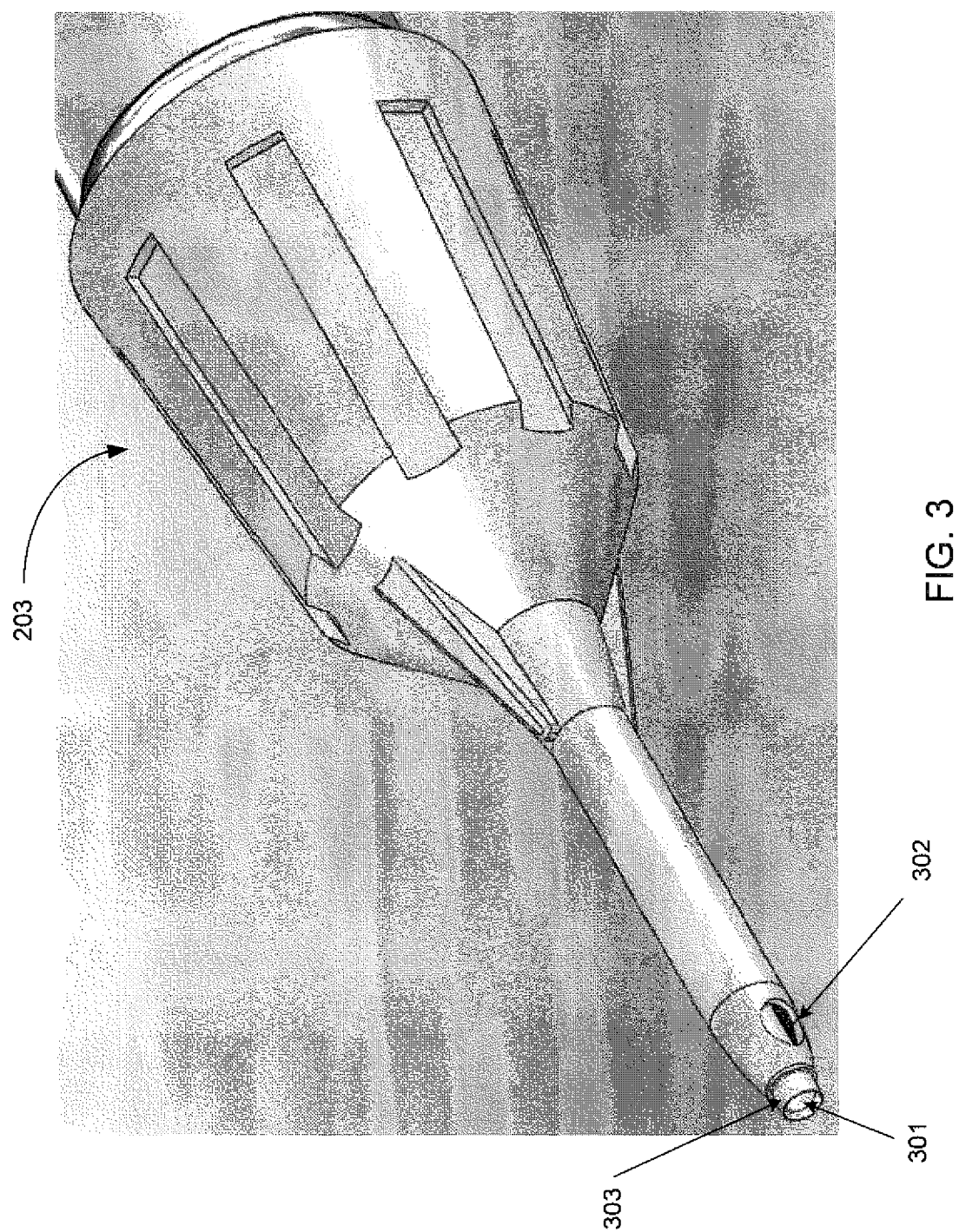
FIG. 3 is an alternate view of a handpiece that may be employed with the present design.

FIG. 3 illustrates a perspective view of the sleeve 203. The needle 301 can be seen through port 302 in this view. The needle 301 moves through opening 303 and is employed to break up the cataract. Port 302 is located on one side of the sleeve 203, while a second port is not shown but is located on the other side of the sleeve 203. Multiple ports may be provided, including more than two ports, while still within the scope of the present invention.

Figure 4:
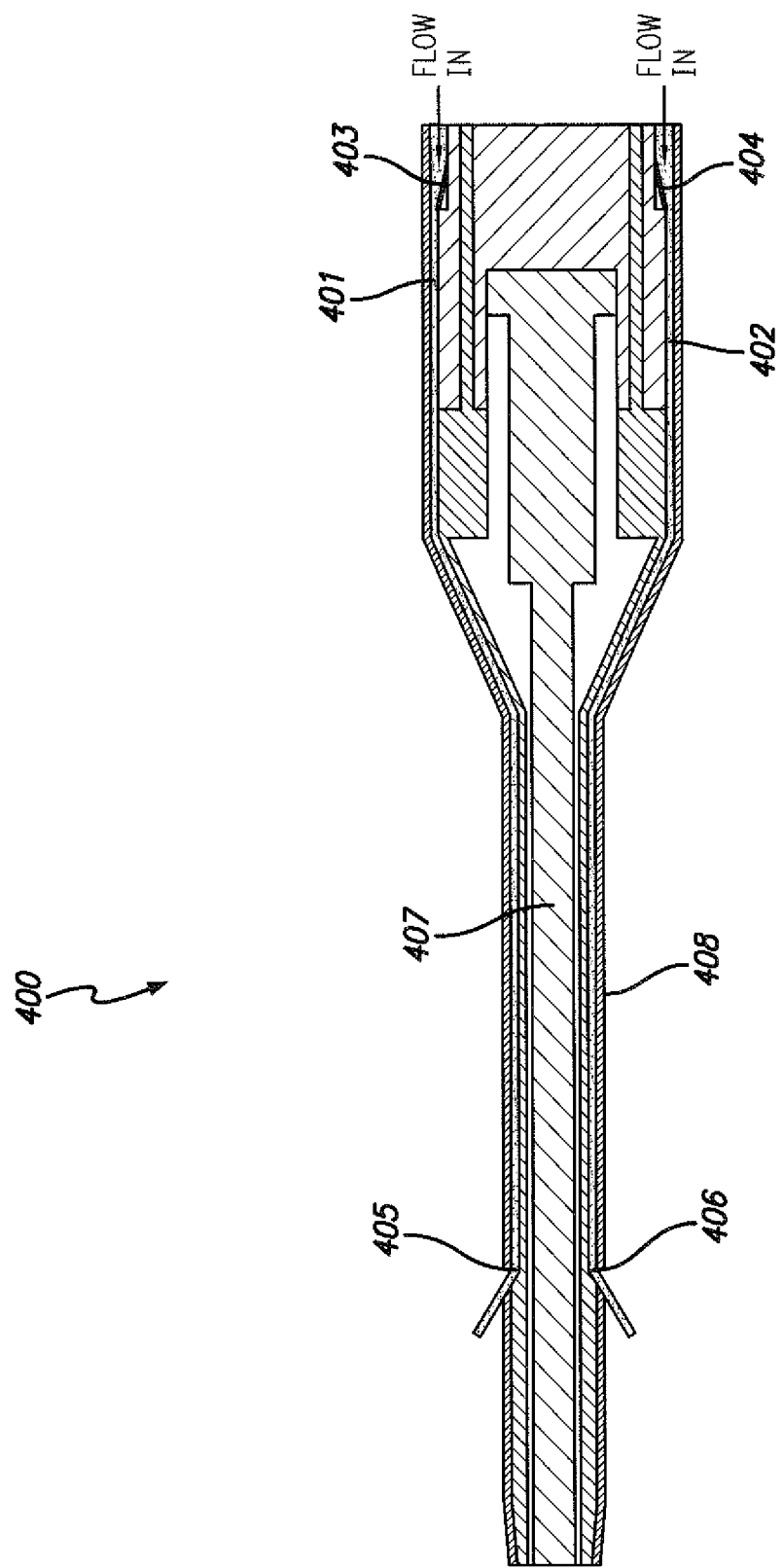
FIG. 4 is a representative view of a handpiece having two fluid flow restrictors in accordance with one embodiment of the present design.

FIG. 4 is a conceptual representation of the handpiece 400 presented to show, among other attributes, fluid flow in the present design. In FIG. 4, the fluid input is provided via lines 401 and 402. The two lines may be separately fed, or more typically a single fluid line may be provided to handpiece 400 and the handpiece constructed such that the fluid from the single input line is directed to lines 401 and 402. In this arrangement, fluid passes to the two paths and can be impeded by gates 403 and 404. Gates 403 and 404 are pivoted elements constructed of a durable material, that when closed stop the flow of fluid to the associated line. In FIG. 4, both gates 403 and 404 are fully open, allowing fluid to pass through. Two lines 401 and 402 are shown with a single gate associated with each line. An additional fluid opening or additional fluid openings may be provided in the sleeve or elsewhere on the handpiece, for example to provide a baseline flow from one opening (not shown) in addition to a controllable flow provided using gates 403 and 404. Also, more or less than two gates and lines may also be provided in the handpiece, and position of the openings may differ from those illustrated in FIG. 4. More or fewer lines may also be provided in the handpiece. The goal is to provide a level of differentiation in fluid flow by the handpiece that is controllable by the user.

In FIG. 4, with both gates open, irrigation fluid flows through two channels in the sleeve, thus providing side port irrigation. Such an arrangement aids in keeping particles centered near the tip of needle 407. Fluid flows into the handpiece as shown, flowing through lines 401 and 402 with gates 403 and 404 open in the configuration of FIG. 4. Once fluid passes through lines 401 and 402, the fluid flows out of ports 405 and 406 in sleeve 408.

When the user desires to change the flow of the FIG. 4 design, she may provide control input causing at least one of the gates 403 and 404 to at least partially close. Surgeon control methodology is discussed below, with one method for providing control using a dual axis footpedal. The surgeon may engage the device to partially close one gate, decreasing flow through the associated opening, or may elect to completely close one gate, such as gate 403, thus closing the flow of fluid, or may partially close gate 403, decreasing the amount of fluid flow. As may be appreciated, when the gates 403 or 404 are closed, the fluid connection preferably does not allow any fluid to flow, i.e. is preferably sealed or watertight. Various gaskets or other devices known in the art may be employed to keep fluid from flowing when a gate is closed.

Gates may be biased in a closed or open orientation. In the example of FIG. 4, the gates are assumed biased open allowing fluid to flow through. Subsequently engaging gate 403 results in a narrowing of the opening and a relatively small fluid flow coming from opening 405 and a large or unabated fluid flow coming from opening 406. This flow differential enables the user to move unwanted ocular material in a desired direction. Note that both gates 403 and 404 can be partially or completely closed at any time, altering flow as desired.

While FIG. 4 and various other figures in the present design show the use of gates, any type of flow restriction device may be employed that inhibits fluid flow through an available fluid channel. Devices such as pinch valves or other pinch mechanisms configured to compress deformable tubes, or other known mechanisms for inhibiting fluid flow may be employed. Such devices may be referred to generally as fluid flow restrictors, where a gate as shown in FIG. 4 is one example of a fluid flow restrictor.

Figure 5:
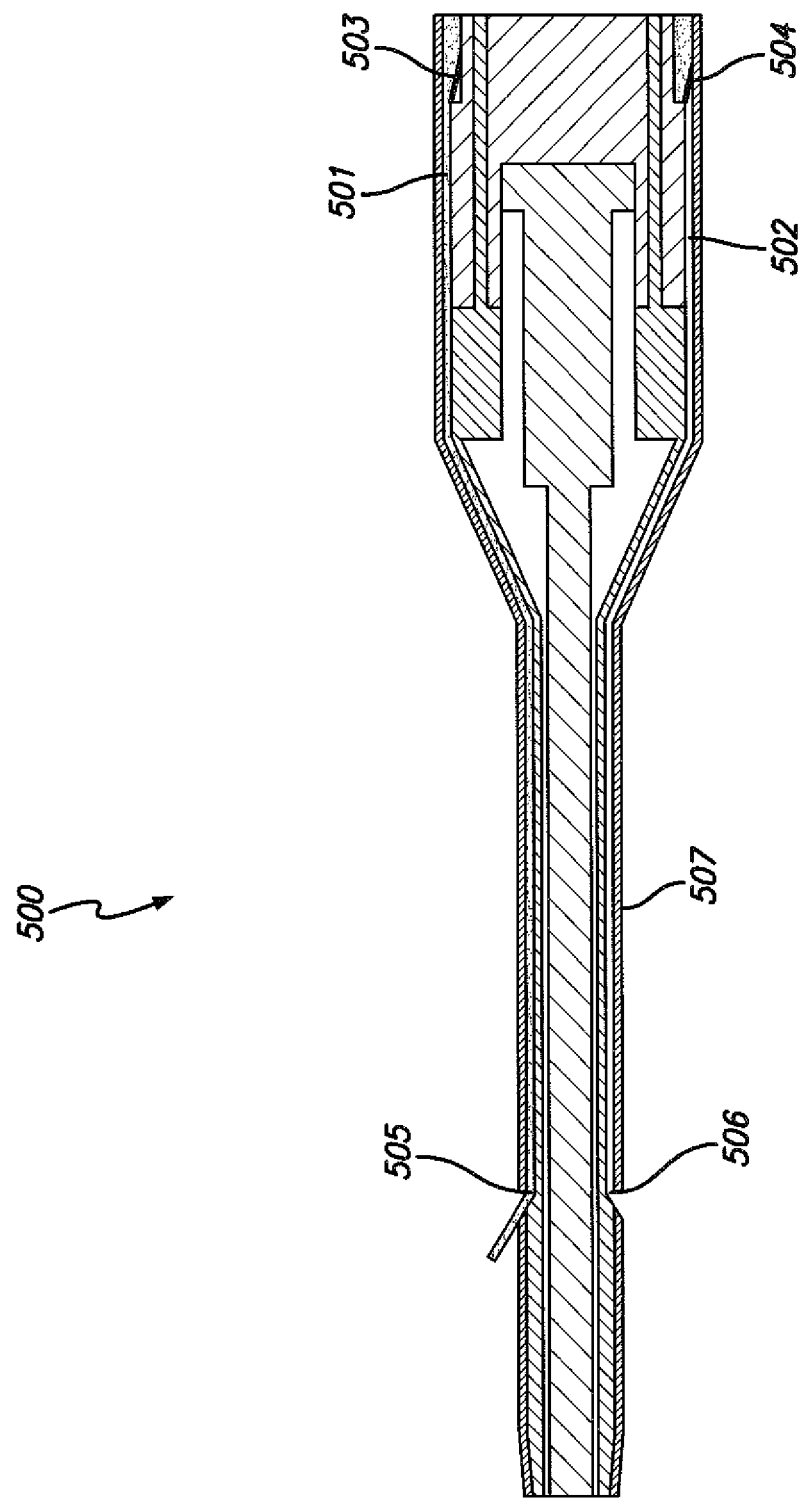
FIG. 5 shows an alternate view of the handpiece similar to that of FIG. 4 with one fluid restrictor open and one fluid flow restrictor closed.
Figure 6:
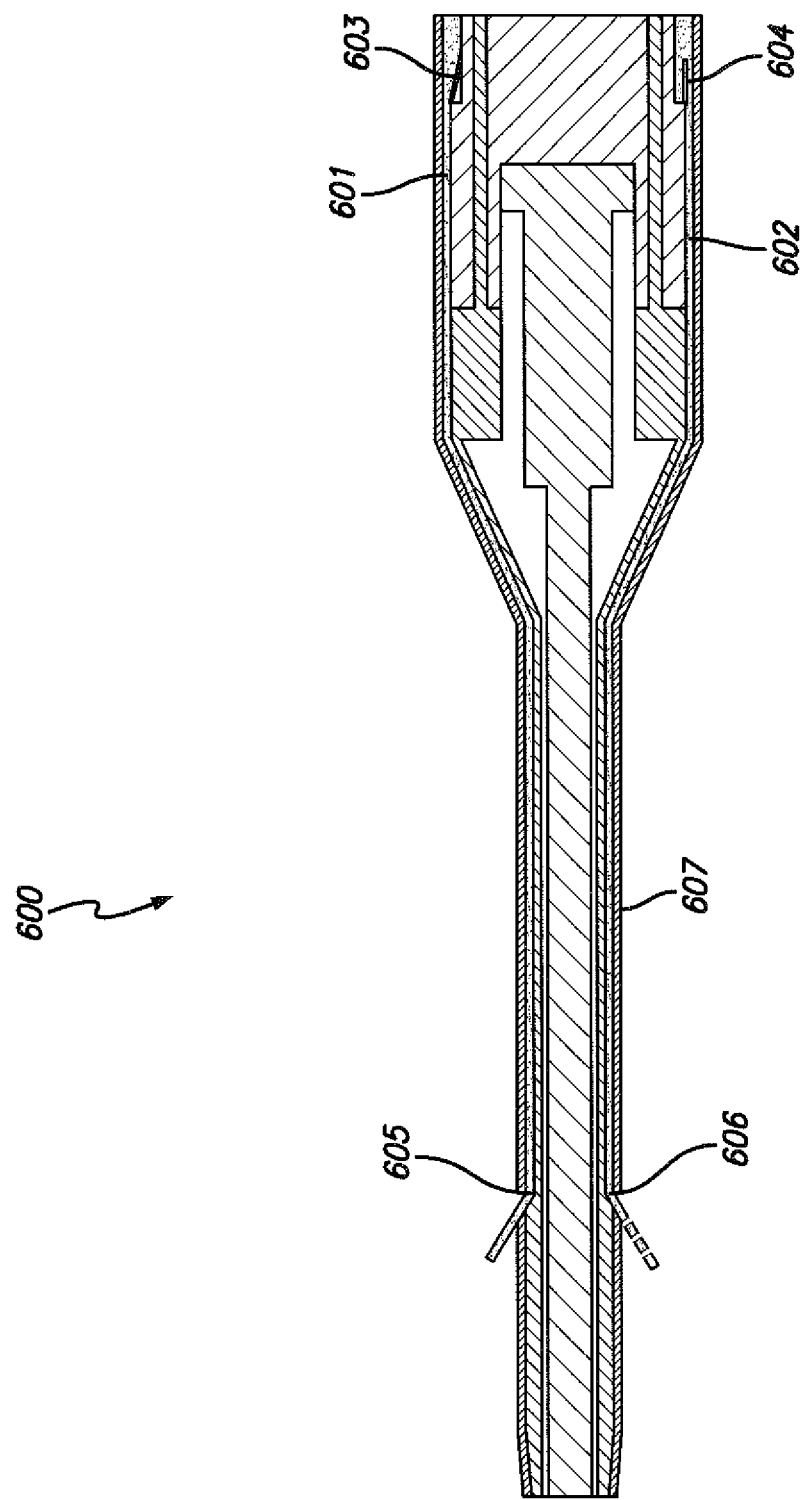
FIG. 6 is a further alternate view of a handpiece similar to that in FIG. 4 with one fluid restrictor fully open and one fluid restrictor partially open.

FIG. 5 illustrates the situation when one gate in the handpiece is closed. From FIG. 5, lines 501 and 502 are provided in handpiece 500, with gates 503 and 504. Gate 504 is closed in FIG. 5, resulting in no flow from opening 506 and flow from opening 505 in sleeve 507. This enables the surgeon to direct irrigation fluid through only one fluid channel in the sleeve, thus providing a bias to the irrigation. FIG. 6 illustrates attenuated dual side port irrigation, where handpiece 600 includes lines 601 and 602. Gate 603 is open in this configuration, with gate 604 partially open. Full irrigation fluid flow emanates from opening 605, while partial fluid flow comes from opening 606 in sleeve 607. The FIG. 6 implementation enables irrigation fluid to be partially or proportionately directed through each available fluid channel in the sleeve 607, thus providing a slight bias to the irrigation. Such an implementation aids in directing particles back toward the center of the ocular chamber without a full bias on one side of handpiece 600.

Figure 7:
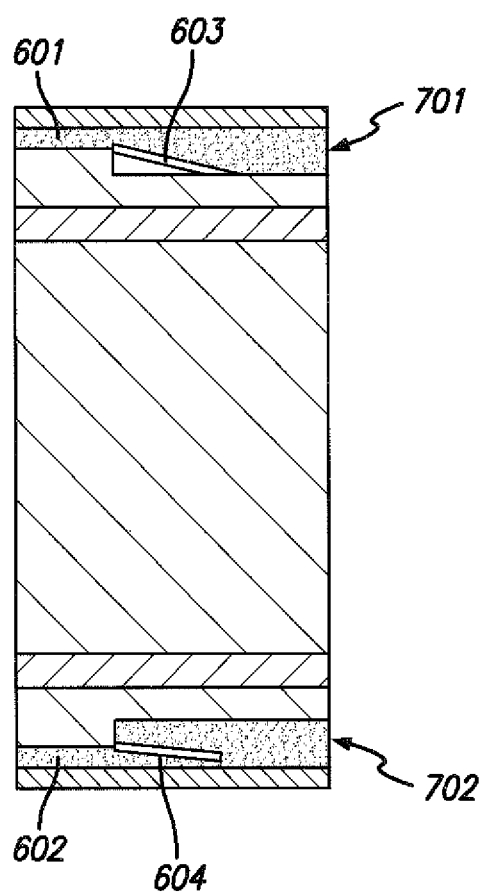
FIG. 7 is an expanded view of the right side of the handpiece shown in FIG. 6 with partial flow through one fluid channel.

FIG. 7 illustrates an expanded view of the right side or proximal part of handpiece 600. As shown in FIG. 7, line 601 is open as gate 603 is in an open position. Fluid coming through incoming line 701 is not impeded and flows into line 601. These fluid lines are referred to as fluid channels. Line 602 is partially open as gate 604 is in a partially open/partially closed state. Fluid coming through incoming line 702 is partially impeded by gate 604 and only part of the fluid flows to line 603. As shown, the gate 604 rotates or pivots about the point closest to the tip of handpiece 600, but other orientations may be employed.

The present design may employ any control method that will enable the surgeon to control the fluid flow in a desired manner. While the foregoing illustrations discuss potential partial control, such as partially opening gates, it is to be understood that control in an on/off or open/closed manner. This on/off type operation provides limited control, but may be implemented using a simple control device such as a button or buttons on the handpiece or footpedal (not shown).

Figure 8:
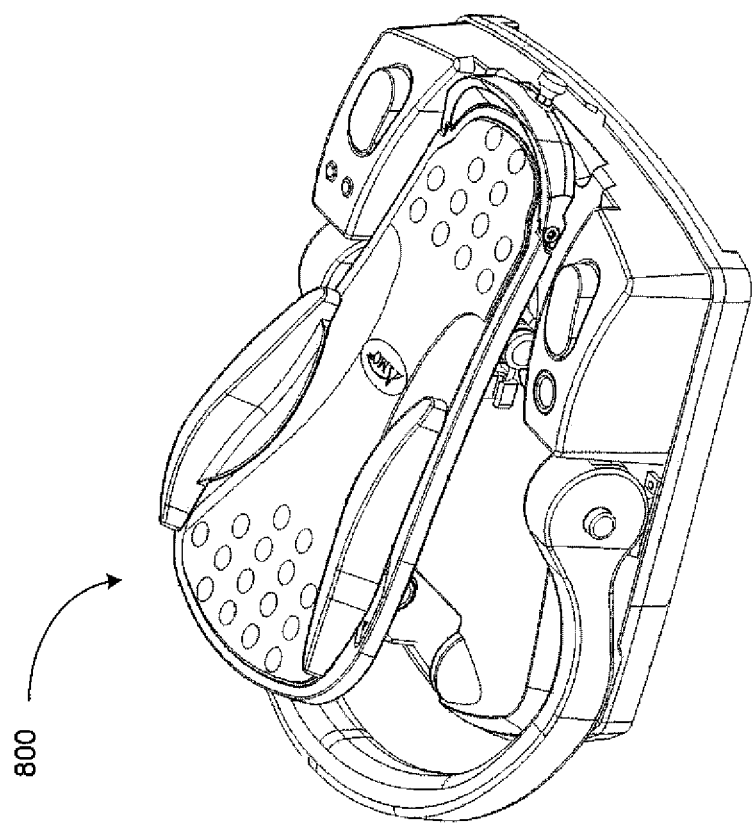
FIG. 8 illustrates an example of a dual axis footpedal that may be employed with the present design.

One other control implementation is the use of a dual axis footpedal such as one shown in FIG. 8. The dual axis footpedal 800 enables movement in a fore-and-aft (pitch) direction and a side-to-side (yaw) direction. The user can control, for example, flow on one side of the handpiece in one axis and flow on the other side of the handpiece with the other axis, such as pitch direction controlling gate 403 and yaw axis controlling gate 404. In this example, the user having his foot off the footpedal 800 results in both gates being open. Movement in the pitch direction would progressively close gate 403, and movement in either yaw direction, left or right, would progressively close gate 404. Other implementations may be realized, such as where the neutral position results in a full fluid flow, i.e. both gates fully open, and shifting in one direction in yaw results in one gate, such as gate 403, progressively closing and in the other direction causing the other gate to close, such as gate 404. In this example, the pitch axis would provide no control. Such an implementation would require one gate to be fully open throughout the procedure. Other control implementations using footpedal 800, or a different type of footpedal such as a single axis footpedal with or without footpedal switches, may be realized.

Various footpedal devices have been used to control an ophthalmic or phacoemulsification/vitrectomy surgical apparatus. Footpedal systems, such as that described in U.S. Pat. No. 4,983,901 provide for a virtually unlimited number of control variations and modes for operating phacoemulsification apparatuses. Additional single linear and dual linear foot pedal patents include U.S. Pat. Nos. 5,268,624; 5,342,293; 6,260,434; 6,360,630; 6,452,120; 6,452,123; and 6,674,030.

In operation, footpedal 800 is connected to instrument host 102 of phacoemulsification/vitrectomy system 100. Instrument host 102 may include logic or software effectuating fluid flow in handpiece 400 as described herein, namely opening or closing available gates in a manner desired. Instrument host 102 provides a connection to handpiece 400, for example, and gates 403 and 404 such that the gates may be opened and closed based on input from the footpedal 800. The ability to set control parameters may be provided, such as a surgeon desiring a right yaw movement to close gate 404 and a left yaw movement to close gate 403, with varying pitch ranges having different gate movement characteristics. For example, a nonlinear profile may be provided, such as a zero to 25 percent footpedal yaw position being linear from zero to 25 percent gate closure, 25 to 75 percent footpedal yaw position corresponding to 50 percent gate closure, and 75 to 100 percent footpedal yaw position again being linear between 75 and 100 percent. The user may have a profile accessible to or receivable by instrument host 102 such that his desired settings may be employed.

In a case where alternate gate and fluid line embodiments are provided, such as in the case of three or four gates, control using a dual linear footpedal such as shown in FIG. 8 may be altered. Depending on circumstances, in a three gate arrangement, control may be provided in a manner such as the pitch axis controlling one channel from completely open to completely closed, with the yaw axis controlling the other two channels, such as yawing to the left controlling a second channel from full open at the center position to full closed at the far left extreme position, and yawing to the right controlling the third channel from full open at the center position to full closed at the far right extreme position.

Other implementations are possible, and options may be provided to the surgeon for preferred control using the footpedal. One alternate embodiment employs a single axis footpedal having foot switches engageable by the surgeon. Foot switches provide not only on/off functionality, but also may provide for incremental increases and/or decreases for each foot tap by the surgeon. For example, the foot pedal may provide for a flow rate, with the neutral position representing full flow and fully depressed representing minimal or zero fluid flow. One or more footpedal switches may be employed by, for example, tapping on one footpedal switch to close one gate a certain amount thereby biasing flow in one direction, where the other foot pedal may enable the surgeon to decrease the amount of bias in that direction. Alternately, the second switch may bias in a different direction, such as in an opposite direction from the bias provided by the first switch. In such a situation, a reset may be provided, such as via an additional switch, or the switches may be programmed to begin opening a gate after a maximum number of taps has occurred.

When a fourth channel is employed, control may be paired between two channels. One four channel orientation provides two fluid exits on opposite sides of the handpiece with two gates uniformly controlled and two separate fluid exits generally ninety degrees from the first channels. Considering the view of the handpiece looking straight on at the tip, the four fluid exits may be positioned at zero degrees, 90 degrees, 180 degrees, and 270 degrees, with the zero and 180 degree ports or openings having channels attached thereto that are uniformly controlled, such as by using the pitch axis of the footpedal 800, with the 90 and 270 degree ports controlled using the yaw axis of footpedal 800. Other implementations may be employed.

While operation has been described with single gate or fluid flow restrictor operation control using movement along one axis in a footpedal or using one variable in a control device, alternate implementations are possible. As an example, a neutral setting may result in a 50 percent fluid flow rate to or from one port and 50 percent fluid flow to or from another port. When a surgeon yaws the footpedal in one direction, such as left, the flow may increase in one direction with an equal decrease in the other direction, effectively providing 75 percent/25 percent or zero percent/100 percent fluid flow.

While discussed herein primarily with respect to irrigation, the present design may be employed for aspiration in general and differential directional aspiration in particular. In such an arrangement, two handpieces may be provided, wherein one handpiece provides irrigation and ultrasonic power to a needle and the other handpiece is used for aspiration. In the alternative, one handpiece may control the ultrasonic power and aspiration while the other handpiece is used for irrigation. Again, multiple fluid channels may be provided, with fluid flow restrictors employed to partially or completely inhibit aspiration of the fluid from the ocular region through the port and out via the fluid channel. Differential control may be provided using a control device such as a footpedal, but when two handpieces are provided, either multiple input or control devices must be provided or simple control may be provided, such as only one fluid flow restrictor in one handpiece (e.g. one irrigation fluid flow restrictor) being controlled by movement in the pitch direction of the footpedal and the other handpiece having one fluid flow restrictor (e.g. one aspiration fluid flow restrictor) controlled by movement of the footpedal in the yaw axis. More than one fluid flow restrictor may be controlled by the control device, either in concert or separately.

One alternative embodiment comprises providing flow out the distal tip of the handpiece when the handpiece takes the form of the handpiece of FIGS. 2 and 3. In this arrangement, constant flow is provided out a distal channel (not shown) created by the needle 301 and sleeve 203. In this embodiment, a device such as a footpedal may be employed to control fluid flow and/or change direction of flow in a manner similar to the use of gates in lines similar to lines 401 and 402.

Thus the present design may include a system host and a control device connected to the system host. The medical system further includes a handpiece having a sleeve with a port opening configured to enable fluid to pass there through, a fluid channel connected to the port opening, and a fluid flow restrictor configured to restrict fluid flow of the fluid channel through the port opening. The control unit is configured to receive input from a user and control an amount of fluid provided by the fluid flow restrictor based on the input received from the user. In one aspect, the medical system is a phacoemulsification system, the handpiece a phacoemulsification handpiece, and the control device a footpedal.

What has been described above includes examples of one or more embodiments. It is, of course, not possible to describe every conceivable combination of components or methodologies for purposes of describing the aforementioned embodiments, but one of ordinary skill in the art may recognize that many further combinations and permutations of various embodiments are possible. Accordingly, the described embodiments are intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A medical system comprising:
    a system host device;
    a handpiece connected to the system host device comprising:
        a sleeve having a first port opening and a second port opening, wherein the first port opening and the second port opening independently dispense fluid therethrough,
        a first fluid channel connected to the first port opening,
        a second fluid channel connected to second port opening,
        a first fluid flow restrictor that variably restricts irrigation fluid flow through the first fluid channel independent of a pressure of the fluid at the first fluid flow restrictor;
        a second fluid flow restrictor that variably restricts irrigation fluid flow through the second fluid channel independent of a pressure of the fluid at the second fluid flow restrictor; and
    a controller connected to the system host device;
    wherein the system host device comprises instructions that when executed cause the system host to provide signals to the handpiece to electronically and individually control the first fluid flow restrictor and second fluid flow restrictor to control the direction of the fluid flow through the first fluid channel and the second fluid channel based on input received at the controller from a user.

2. The medical system of claim 1, wherein the first fluid flow restrictor comprises a hinged gate type mechanism configured to open and close based on signals received from the system host device.

3. The medical system of claim 1, wherein the controller is a dual axis footpedal.

4. The medical system of claim 1, wherein the controller is a footpedal, and signals received from the footpedal are employed by the system host to cause a bias in the amount of fluid provided by the first fluid channel and the second fluid channel.

5. The medical system of claim 3, wherein one axis of the footpedal is configured to control the first fluid flow restrictor and an alternate control input is configured to control the second fluid flow restrictor.

6. The medical system of claim 1, wherein the medical system is a phacoemulsification system and the handpiece is a phacoemulsification handpiece.

7. A handpiece configured for use in a medical system, comprising:
    a sleeve comprising a first port opening and a second port opening, wherein the first pot opening and the second port opening independently dispense fluid therethrough;
    a first fluid channel disposed within the handpiece and connected to the first port opening a second fluid channel disposed within the handpiece and connected to the second port opening;
    a first fluid flow restrictor disposed within the handpiece that variably restricts irrigation fluid flow through the first fluid channel independent of a pressure of the fluid at the first fluid flow restrictor; and
    a second fluid flow restrictor disposed within the handpiece that variably restricts irrigation fluid flow through the second fluid channel independent of a pressure of the fluid at the second fluid flow restrictor;
    wherein the handpiece:
    receives a signal from a control unit, wherein the signal is based on an input from a user, and electronically and individually controls a degree of opening of the first fluid flow restrictor and the second fluid flow restrictor to control the direction of the irrigation fluid flow through the first fluid channel and the direction of the irrigation fluid flow through the second fluid channel based on the signal.

8. The handpiece of claim 7, wherein the first fluid flow restrictor comprises a hinged gate type mechanism configured to open and close based on signals received from the control unit.

9. The handpiece of claim 7, wherein the control unit comprises a dual axis footpedal.

10. The handpiece of claim 7, wherein the control unit comprises a footpedal, and the handpiece is configured to receive signals from the footpedal and control the first fluid flow restrictor and the second fluid flow restrictor based on the signals received from the footpedal.

11. The handpiece of claim 9, wherein:
    the first fluid flow restrictor is controlled based on movement of the footpedal along a first axis; and
    the second fluid flow restrictor is controlled based on a state of an alternate input mechanism provided with the footpedal.

12. The handpiece of claim 7, wherein the handpiece is a phacoemulsification handpiece.

13. A medical system comprising a system host and a control device connected to the system host, the medical system further comprising:
    a handpiece communicatively connected to the system host, comprising:
        a sleeve comprising a first port opening and a second port opening,
    wherein the first port opening and the second port opening independently dispense fluid therethrough,
        a first fluid channel disposed within the handpiece and connected to the first port opening,
        a second fluid channel disposed within the handpiece and connected to the second port opening,
        a first fluid flow restrictor disposed within the handpiece that variably restricts irrigation fluid flow through the first fluid channel independent of a pressure of the fluid at the first fluid flow restrictor; and
        a second fluid flow restrictor disposed within the handpiece that variably restricts irrigation fluid flow through the second fluid channel independent of a pressure of the fluid at the second fluid flow restrictor;

wherein the control device:
receives input from a user, and
generates a control signal based on the input to control an amount of irrigation fluid and direction of irrigation fluid dispensed by the first port opening and the second port opening based on the input received from the user;

wherein the handpiece:
receives the control signal, and
electronically and individually controls a degree of opening of the first fluid flow restrictor and the second fluid flow restrictor, respectively, to control the amount of irrigation fluid and direction of the irrigation fluid flow through the first fluid channel and the amount of irrigation fluid and direction of the irrigation fluid flow through the second fluid channel based on the control signal.

14. The medical system of claim 13, wherein the first fluid flow restrictor comprises a hinged gate type mechanism configured to open and close based on signals received from the control device.

15. The medical system of claim 13, wherein the control device comprises a footpedal.

16. The medical system of claim 13, wherein the control device comprises a dual axis footpedal, and the handpiece further:
receives signals from the footpedal, and
controls the first-fluid flow restrictor and the second flow restrictor based on the signal from the footpedal.

17. The medical system of claim 15, wherein:
the first fluid flow restrictor is controlled based on movement of the footpedal along a first axis; and
the second fluid flow restrictor is controlled based on a state of an alternate input mechanism provided with the footpedal.

18. The medical system of claim 13, wherein the medical system is a phacoemulsification system and the handpiece is a phacoemulsification handpiece.

19. A medical system comprising:
a system host device;
a handpiece connected to the system host device comprising:
a sleeve having a first port opening and a second port opening wherein the first port opening and the second port opening independently dispense fluid therethrough,
a first fluid channel connected to the first port opening,
a second fluid channel connected to the second port opening,
a first fluid flow restrictor that restricts irrigation fluid flow through the first fluid channel, and
a second fluid flow restrictor that restricts irrigation fluid flow through the second fluid channel; and
a controller communicatively connected to the system host device;
wherein the system host device comprises instructions that when executed cause the system host to provide signals to the handpiece to electronically and independently control the first fluid flow restrictor and the second fluid flow restrictor to control the direction of the fluid flow through the first fluid channel and the direction of the fluid flow through the second fluid channel based on input received at the controller from a user, and wherein the control of the first fluid flow restrictor and second fluid flow restrictor is independent of a pressure of the fluid flow through the first fluid channel and the second fluid channel.

20. The handpiece of claim 7, wherein the handpiece is configured to control a degree of restriction imposed on the irrigation fluid by the first fluid flow restrictor and the second fluid flow restrictor based on the signal.

21. The handpiece of claim 7, wherein the first fluid flow restrictor is configured to change degree of opening through which the irrigation fluid flows based on the signal, and
wherein the second fluid flow restrictor is configured to change degree of opening through which the irrigation fluid flows based on the signal,
wherein the first fluid flow restrictor and the second fluid flow restrictor are independently controlled.

22. The handpiece of claim 21, wherein the degree of opening includes fully closed, fully open, and partially open.

* * * * *